US006780508B1

(12) United States Patent
Caponetti et al.

(10) Patent No.: US 6,780,508 B1
(45) Date of Patent: Aug. 24, 2004

(54) POWDER PARTICLES WITH SMOOTH SURFACE FOR USE IN INHALATION THERAPY

(75) Inventors: Giovanni Caponetti, Parma (IT); Pier Luigi Catellani, Parma (IT); Ruggero Bettini, Parma (IT); Paolo Colombo, Parma (IT); Paolo Ventura, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 10/030,686

(22) PCT Filed: Jul. 13, 2000

(86) PCT No.: PCT/EP00/06690

§ 371 (c)(1),
(2), (4) Date: Apr. 16, 2002

(87) PCT Pub. No.: WO01/05429

PCT Pub. Date: Jan. 25, 2001

(30) Foreign Application Priority Data

Jul. 16, 1999 (IT) .......................................... MI99A1582

(51) Int. Cl.[7] ................................................. B32B 5/16
(52) U.S. Cl. ........................ 428/403; 428/407; 424/45; 424/46; 424/434; 424/435; 424/489; 424/493; 514/2; 514/3; 514/21; 514/23; 514/167; 514/523; 514/165; 514/456
(58) Field of Search ................................ 428/403, 407; 424/45, 46, 434, 435, 489, 493; 514/2, 3, 21, 23, 167, 529, 169, 456

(56) References Cited

U.S. PATENT DOCUMENTS

| 4,349,542 A | * | 9/1982 | Staniforth ................... 424/679 |
| 5,254,330 A | * | 10/1993 | Ganderton et al. |
| 6,284,287 B1 | * | 9/2001 | Sarlikiotis et al. .......... 424/689 |
| 6,641,844 B1 | * | 11/2003 | Musa et al. ................. 424/489 |

FOREIGN PATENT DOCUMENTS

EP          0 786 526          7/1997

OTHER PUBLICATIONS

Podczeck F: "The Influence. . . Powder Inhalations" A Aerosol Science and Technology, vol. 31, No. 4, 1999 pp. 301–321.*

F. Podczeck: "The influence of particle size distribution and surface roughness of carrier paricles on the in vitro properties of dry power inhalations" Aerosol Science and Technology, vol. 31, No. 4, pp. 301–321.

U.S. patent application Ser. No. 10/628,453, Musa et al, filed Jul. 29, 2003.

U.S. patent application Ser. No. 10/030,686, Caponetti, filed Jan. 16, 2002.

* cited by examiner

Primary Examiner—Leszek Kiliman
(74) Attorney, Agent, or Firm—Oblon, Spivak, McClelland, Maier & Neustadt, P.C.

(57) ABSTRACT

Carriers for use in the preparation of mixtures for inhalation powders intended for pulmonary administration of micronized drugs by means of a dry powder inhaler and the method for their preparation are described.

22 Claims, 6 Drawing Sheets

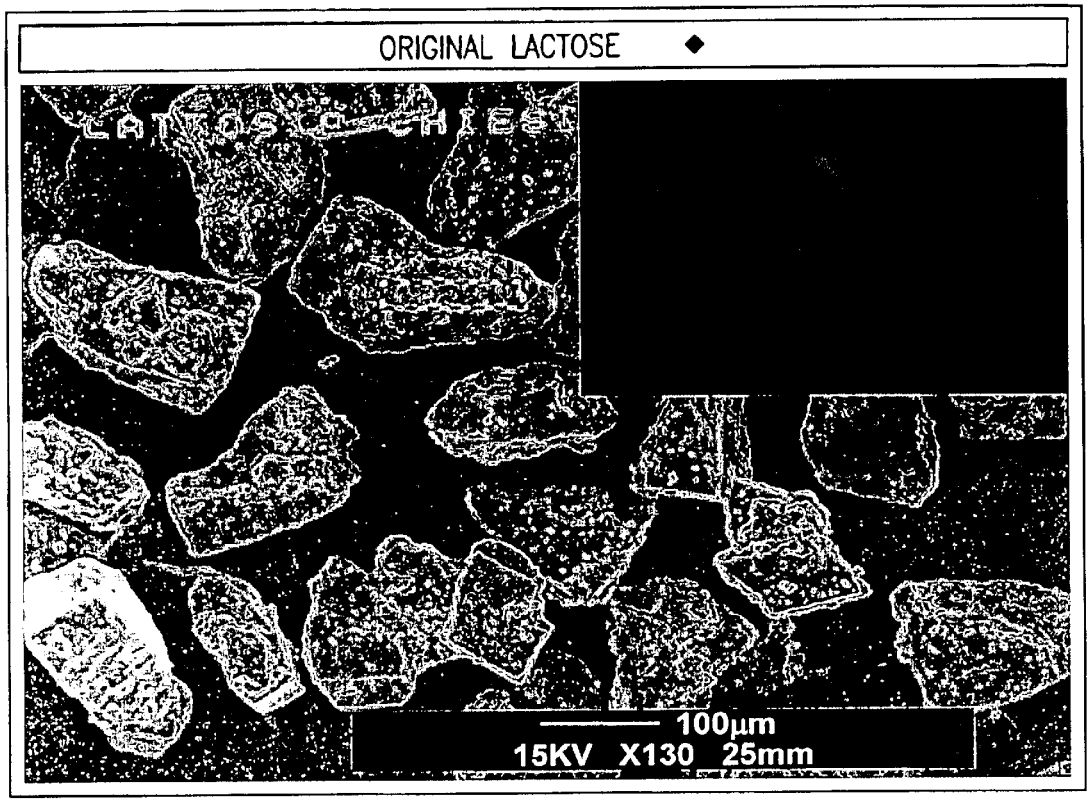
FIG.1a(1)
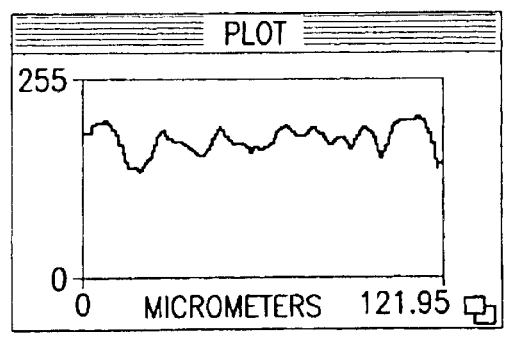
FIG.1a(2)

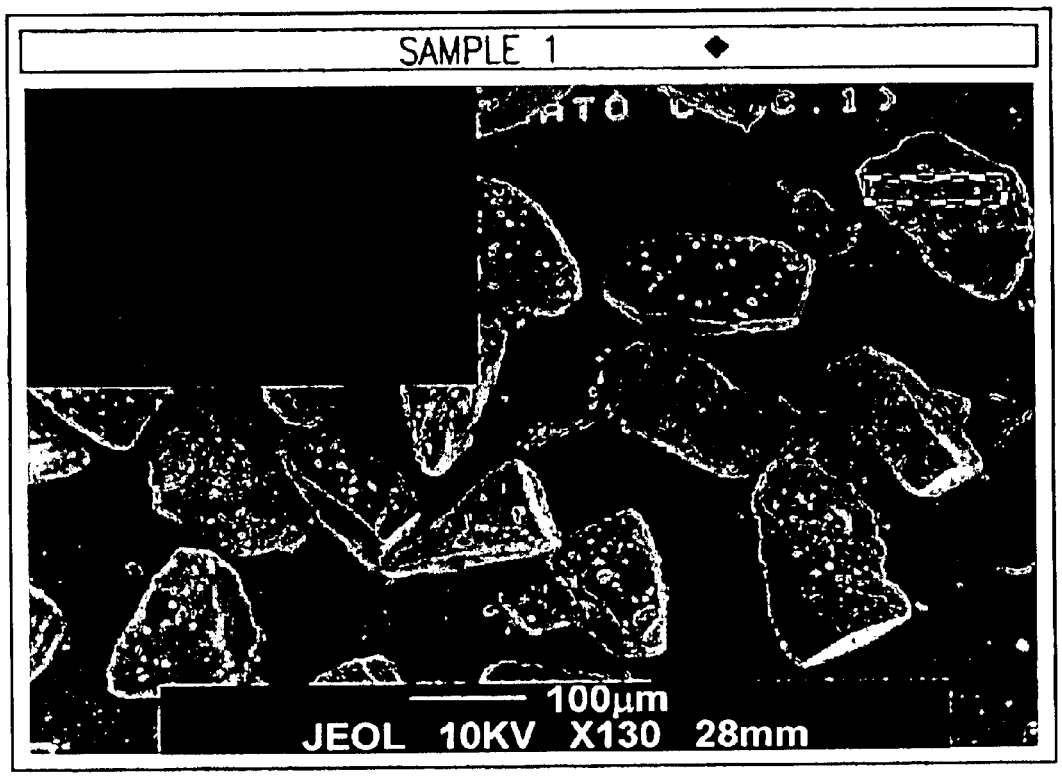
FIG.1b(1)
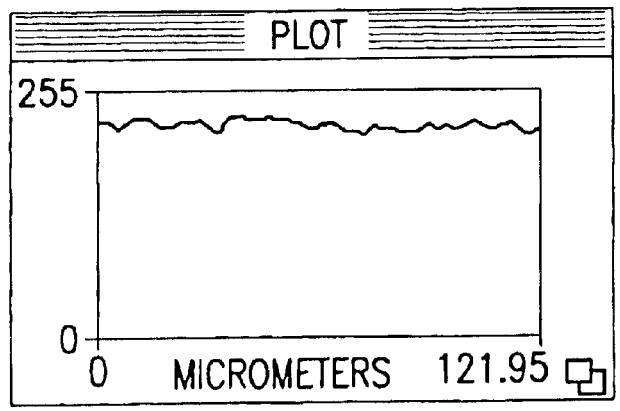
FIG.1b(2)

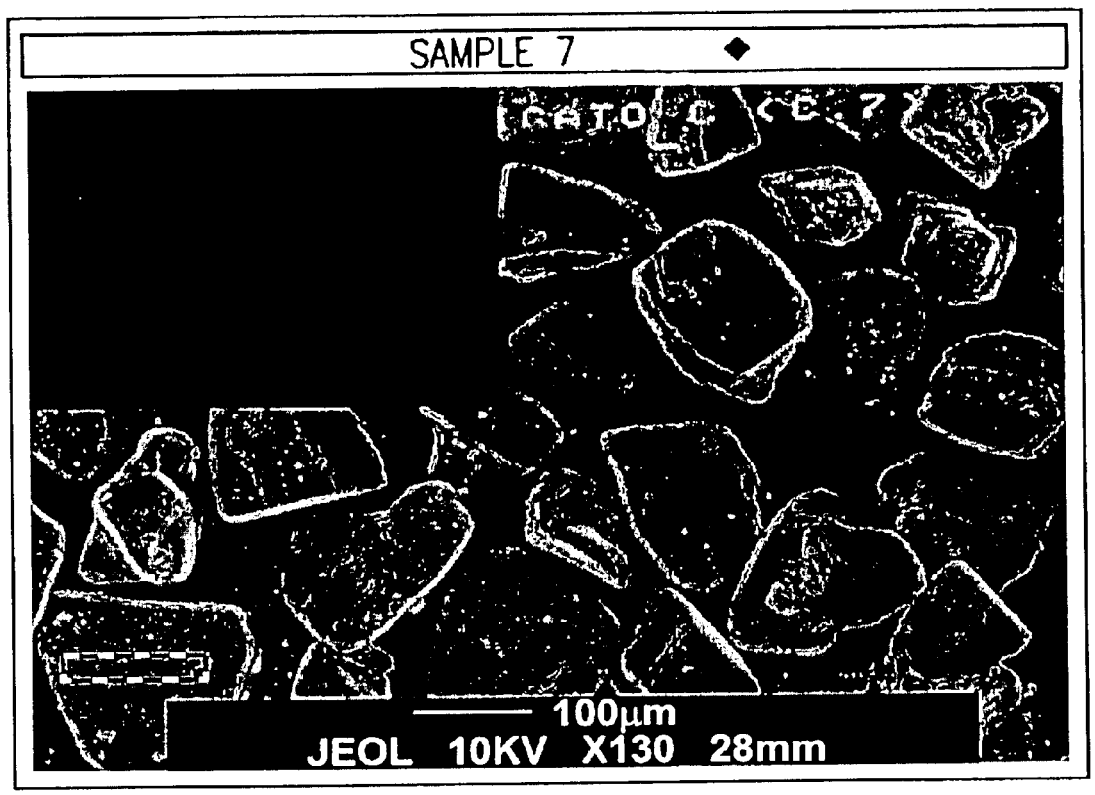
FIG.1c(1)
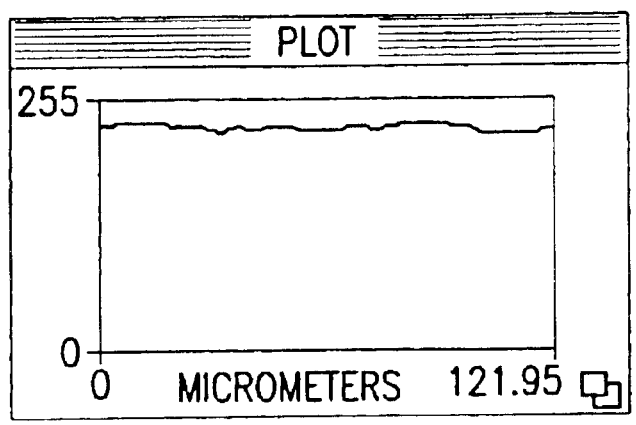
FIG.1c(2)

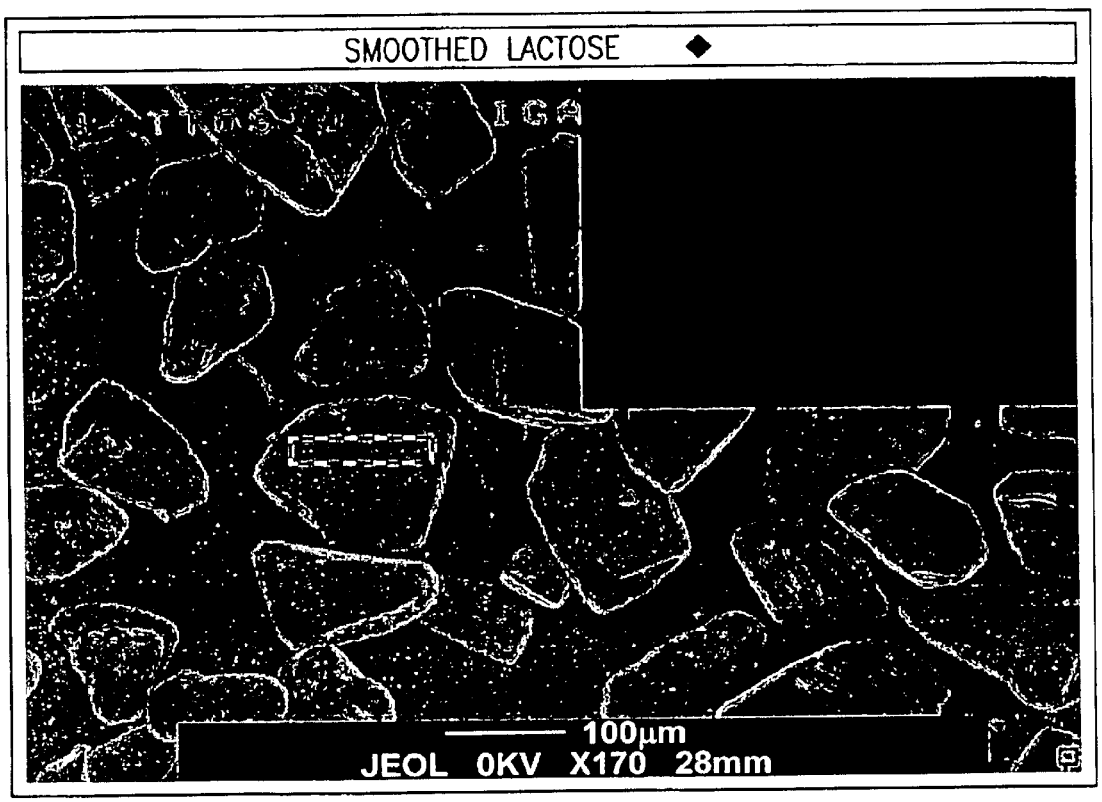
FIG.1d(1)
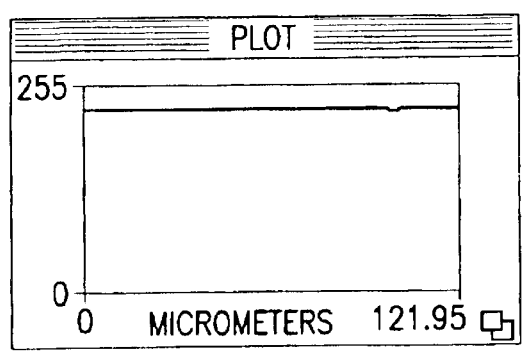
FIG.1d(2)

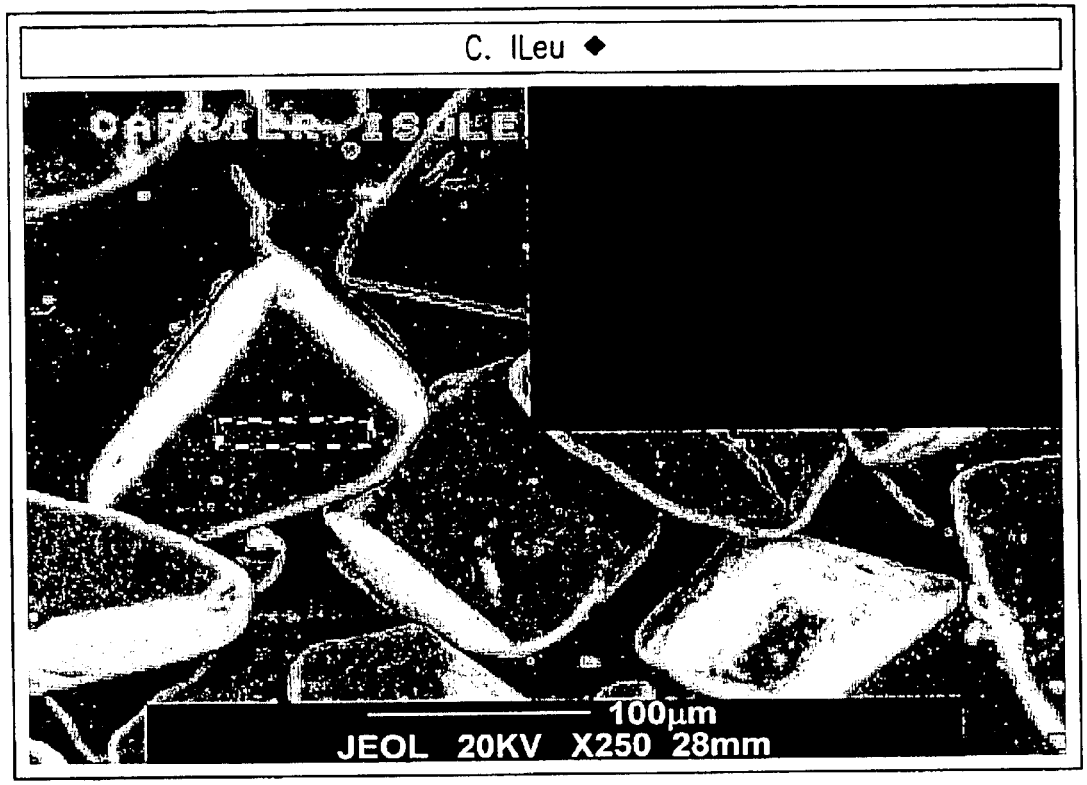
FIG.2a(1)
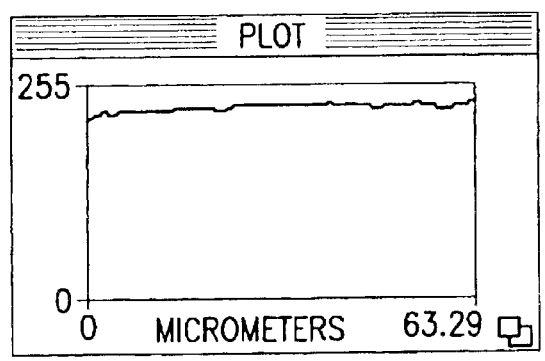
FIG.2a(2)

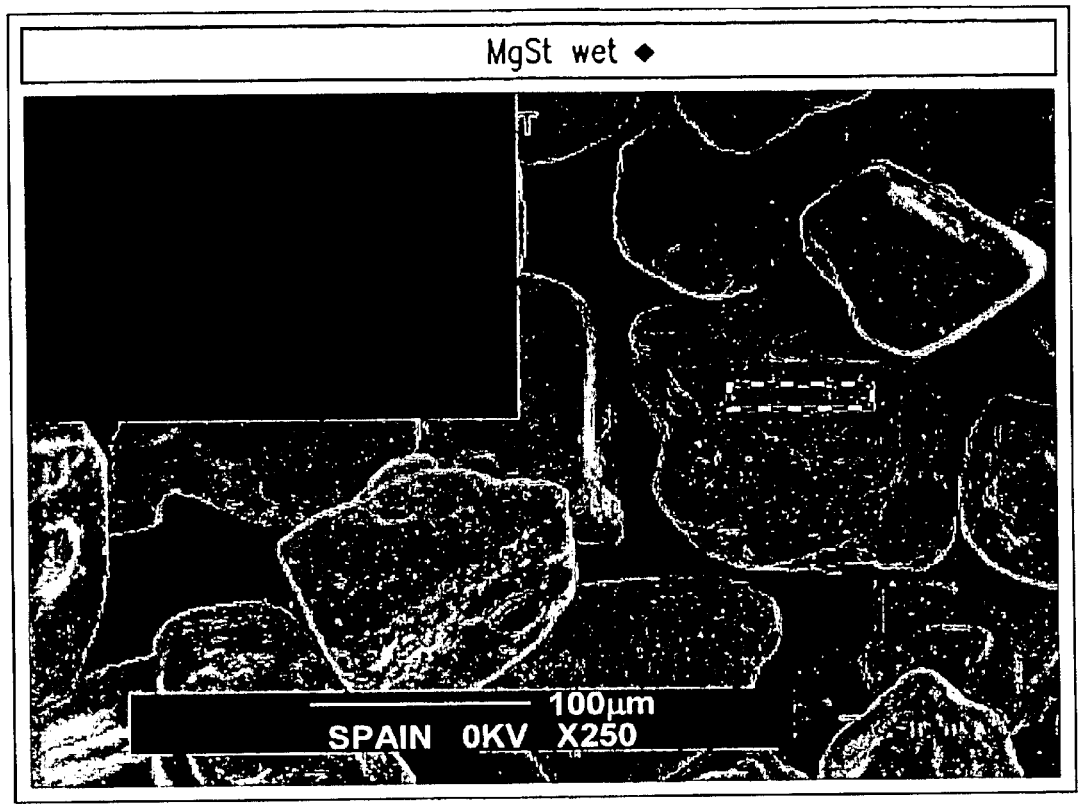
FIG.3a(1)
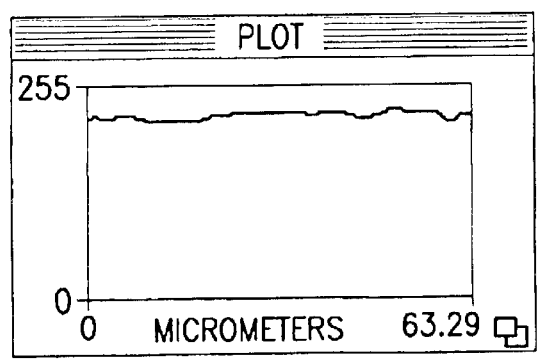
FIG.3a(2)

POWDER PARTICLES WITH SMOOTH SURFACE FOR USE IN INHALATION THERAPY

SUMMARY OF THE INVENTION

The invention relates to carrier particles (the carrier) for use in the preparation of powdery mixtures for inhalation intended for the pulmonary administration of micronized drugs by means of a dry powder inhaler and the method for their preparation.

According to a first aspect, the invention relates to a novel carrier, consisting of a crystalline substance in powder form, in the size range from tens to hundreds of microns, whose particles have a perfectly smooth surface.

A second aspect of the invention relates to a method for smoothing the surface of said particles. The method claimed is able to make the surface of the particles of the carrier smooth, without any roughness, or hollows, clefts and sharp edges, which represent sites of high surface energy to which the drug particles might adhere, without being removed in the aerosol clouds production stage.

The claimed method further permits to improve the uniformity of the surface characteristics of commercially available substances, which are commonly employed as carriers for inhalation powders, whose characteristics are generally rather variable.

Finally, a third aspect of the invention comprises carrier particles that are obtained with the said smoothing method, the surface of which is coated or partially coated with a suitable additive. By virtue of the claimed method the particles of the additive are not released from the carrier particles during inhalation and so do not reach the smaller branching of the pulmonary tree where absorption occurs.

The powders for inhalation obtained by mixing the smooth carrier particles (with or without coating) with a micronized drug give rise to a particularly high respirable fraction of drug.

PRIOR ART

Drugs intended for inhalation therapy, carried out by the administration of dry powders, are characterized by a particle size of a few microns. The particle size is quantified by measuring a characteristic equivalent sphere diameter, known as aerodynamic diameter, which expresses the ability of the particles to be transported as a suspension in an air stream (aerosolization). In general, particles with an aerodynamic diameter of less than 6.4 microns are regarded as respirable, i.e. capable of penetrating into the lungs.

The administration of these drugs in the form of micronized powder requires the use of suitable dry powder inhalers (DPIs).

DPIs in turn can be divided into two basic types:
i) single dose inhalers, for the administration of single subdivided doses of the active compound;
ii) multidose dry powder inhalers (MDPIs), preloaded with quantities of active principles sufficient for longer treatment cycles.

Although micronization of the drug particles is essential for penetration to the deepest branchings of the pulmonary tree during inhalation, it is also known that the finer are the particles, the stronger are the cohesion forces. In multidose inhalers, said effects hamper the loading of the doses of powder from the reservoir system to the aerosolization chamber, since the cohesion forces reduce free flowing of the particles and promote their agglomeration and/or their adhesion to the walls. The aforementioned effects therefore impair the efficiency and reproducibility of the delivered dose and are detrimental to the respirable fraction.

Multidose inhalers work properly when so-called free-flowing powders are used, generally formulated by mixing the micronised drug with a carrier material (generally lactose, preferably α-lactose monohydrate) consisting of coarser particles, approximately equal or greater than 100 microns. In such mixtures, the micronised active particles mainly adhere to the surface of the carrier particles whilst in the inhaler device; on the contrary, during inhalation, a redispersion of the drug particles from the surface of the carrier particles occurs allowing the formers to reach the absorption site into the lungs.

Mixing with the carrier also facilitates the introduction and withdrawal of the inhalation preparation, in a regular dose, from the reservoir of a multidose inhaler or its dosage in single-dose containers. Mixing of the micronized drug with the coarse carrier therefore leads to the production of a mixture in which the micronized drug is distributed uniformly on the carrier particles as a result of the interactions, usually of an electrostatic nature, which establish between the drug particles and the carrier particles. Said interactions lead to the production of a so-called ordered mixture. It is extremely important for the interactions to be weak and reversible, so that, since transport in the air stream and the respirability of the powder depend on the particle size, only the micronized drug particles will be able to be deposited in the lungs, whereas the coarser carrier particles will be deposited, because of their mass, in the upper airways. Due to the weak interactions between the two components of the mixture, breathing-in through the inhaler causes separation of the micronized drug particles from the coarse carrier particles and therefore inhalation of the smaller particles and deposition of the coarser particles in the oropharyngeal cavity. Accordingly, it is of great applicative interest to find new carriers for inhalers and new techniques for the production of drug-carrier mixtures easy to handle and able to generate a high respirable fraction.

The use of a carrier is indeed not free of drawbacks in that the strong interparticle forces between the two ingredients may prevent the separation of the micronised drug particles from the surface of the coarse carriers ones on inhalation, so compromising the availability of the drug to the respiratory tract.

In the prior art there are many examples of processes for modifying the surface conditions of the carrier with the aim of reducing the strength of the interactions between the particles during inhalation, without causing pre-separation of the drug particles in the inhaler.

Ganderton (BG 2 240 337) reports that the surface conditions of the particles, in particular their rugosity, are critical for the behaviour of the carrier during inhalation and claims pharmaceutical carriers, such as lactose, consisting of particles whose rugosity is controlled by a cristallization process. The rugosity of the said particles is evaluated using measurements of surface area, based on gas permeametry. The surface area value measured by this technique, relative to the theoretical surface area value, provides a numerical index of rugosity called Ganderton scale.

It is known anyway that measurements based on the said parameter (gas permeametry) only provide reliable data in the case of powders consisting of particles with diameter below 45 μm (subsieve range). In fact, by using such method, no difference between the lactose before and after the smoothing treatment can be detected in the case of particles with a mean diameter of about 100 μm. Moreover the values obtained are not reliable (≈2.5) as demonstrated in Example 1.

In any case, the method of the prior art makes it possible only to reduce the surface rugosity of the carrier particles, as they can have a degree of surface rugosity up to 1.75, determined according to the permeametry method.

Staniforth (WO 95/11666) claims a milling process preferably carried out in a ball mill, called corrasion (for analogy with the effect of wind on rocks), which alters the surface characteristics of the carrier by removing asperities in the form of small grains; these grains in turn can become attached to the clefts of the surface area of the particles, so saturating the high-energy sites. As a result of this preliminary treatment of the carrier, the micronized drug particles are deposited preferentially on lower-energy sites and so are subject to weaker forces of interparticle adhesion.

It is also known from the literature that various types of commercial lactose can have a moderate degree of surface rugosity.

In Kawashima et al. (Int J Pharm 172, 1998, 179–188) examples are given of crystalline lactose with rugosity between 1.33 and 1.13, evaluated on the basis of the perimeter of the particles determined by scanning electron microscope (scale utilized by Kawashima).

Podczeck F (J Adhesion Sci Technol 12, 1998, 1323–1339) reports that Pharmatose 125 M (a commercially available lactose) is characterized by a surface rugosity, expressed in μm, of 1.12±0.74 (scale utilized by Podczeck).

The values reported relate however to batches of lactose with a granulometric distribution between approx. 30 and 90 μm and characterized by a median diameter of approx. 60 μm. It is known, however, that the finer the particles, the more they have a regular shape and so are intrinsically characterized by a lower rugosity value.

On the other hand, the operation of some multidose inhalers requires the use of optimum carriers of high flowability, a characteristic that can only be imparted by using particles with a greater granulometric distribution.

Disaggregation of the active principle from the carrier during inhalation can also be made more efficient by addition of a fraction of fine particles of the same carrier. The Boheringer patent EP 0 663 815 claims the use of carriers for controlling and optimizing the amount of drug released during the aerosolization phase, comprising suitable mixtures of coarse particles with size >20 μm and of fine particles with size <10 μm.

Finally, in the prior art, additives with lubricant, glidant or anti-adherent properties, dry-mixed with the carrier, have been employed with the aim of reducing the forces of attraction between drug and carrier. For example, mixing of magnesium stearate with crystalline lactose is able to reduce the forces of adhesion between drug and carrier, when this mixture is used as inhalation carrier. For explaining the effectiveness of magnesium stearate in the aerosolization of inhalation powders, investigations conducted on powder mixtures for tablets can be taken into account (Staniforth et al., J. Pharm. Pharmacol. 1982, 34, 141–145). These investigations showed that the presence of lubricants causes a decrease in cohesion of the tablets because they form a lubricated layer on the powder particles that are to be pressed together, thereby interfering with the bond between them. This mechanism is also regarded as responsible for the decrease in strength of adhesion of the micronized drug particles on the carrier particles (Kassem, thesis, London University, 1990).

In WO 96/23485, the particles are mixed with a substance with anti-adherent or antifriction properties, consisting of one or more compounds selected from amino acids (in particular leucine), phospholipids or surfactants; deposition of the additive on the carrier is preferably carried out in the dry form, and does not give rise to a complete coating of the carrier, but rather to a discontinuous covering in order to saturate the high-energy sites. Preferably, the carrier particles and the additive are submitted to the corrasion process in a ball mill as described in WO 95/11666.

It follows from examination of the prior art that in the case of an inhalation powder, consisting of a drug-carrier mixture, efficient disaggregation of the active principle from the carrier during inhalation is dependent upon the drug-carrier interparticle forces and so depends on the surface characteristics of the latter.

Furthermore, it has been found in certain cases that commercial batches of lactose obtained from the same manufacturer, though possessing the same physicochemical and technological characteristics, exhibited substantially different behaviours on inhalation, so that they could not be regarded as equivalent. A difference in surface area among these batches can be for instance detected by the multiple-point BET method, even in cases when they could not be appreciated by gas permeametry or by the single-point BET method.

Images obtained with the scanning electron microscope showed, in turn, that this difference was to be ascribed to the different conditions of surface rugosity of the particles.

In the batches of lactose examined, it was also noted that there was a different percentage and granulometric distribution of fine particles.

The presence of fine particles in the lactose for inhalation might be useful for optimizing the respirability of an active principle mixed with a coarse carrier, as claimed in patent EP 0 663 815. However, since only the fine fraction below 10 μm is effectively responsible for the decrease in the interparticle forces, whereas the fraction greater than 10 μm lowers the flowability of the powder, it is important to be able to control the percentage and distribution of the fine particles in accordance to the use the carrier is directed to.

As already observed, the commercially available excipients, being substances widely used in the pharmaceutical field and intended for several applications, exhibit small but substantial variations, e.g. of surface area or distribution of fine particles, which can impair their performance when they are used for particular purposes, such as carriers for inhalation powders.

Although it has been widely reported that by altering the surface characteristics of the carrier it is possible to increase the respirable fraction of the inhaled drug, it has never been previously described a process of treatment of carrier particles for inhalation powders able to eliminate the random variations of the surface characteristics caused by the ordinary manufacturing processes.

OBJECT OF THE INVENTION

It has now been found that by pre-treating the carrier in a high-speed mixer-granulator it is possible to obtain carrier particles with median diameter greater than 90 μm, smooth and homogeneous, characterized by a surface rugosity of less than 1.1, and preferably between 1.0 and 1.1 (fractal scale), suitable for making inhalation powders.

A first aspect of the invention therefore relates to a new type of carrier for inhalation powders, characterized by particles having perfectly smooth surfaces and rounded edges or corners. In these particles, surface rugosity—which often creates problems when using the carriers for the preparation of inhalation powders—has been completely eliminated, making the particles perfectly smooth.

A second aspect of the invention relates to the method of preparation of these carriers consisting of particles with perfectly smooth surface. The claimed method allows to obtain said smooth surface. The claimed method allows to obtain said smooth particles starting from an industrial powder consisting of rough particles, without substantially altering their average size and their geometry.

The carrier of the invention can be prepared using a high-speed mixer-granulator, an apparatus designed and normally used for agglomerating solid particles and not for smoothing them individually. This generally consists of a cylindrical chamber with a chamfered bottom, in which a rotating paddle is inserted, and once this is running at a suitable speed it causes the powder contained within the cylindrical chamber to roll along the chamber walls. The mixing chamber is sealed by a cover, which contains a sprayer for adding liquid, and can operate in controlled conditions of temperature and pressure. Until now, this type of equipment has been used exclusively for the preparation of granules or pellets, i.e. to agglomerate the individual particles, by means of a liquid binder, to give more complex structures, called granules.

It has now been found that in certain conditions, the use of such apparatus allows to alter the surface characteristics and shape of particles of pharmaceutical excipients, such as those proposed as carriers for inhalation powders, without agglomerating them and without significantly changing their crystalline structure and physiocochemical properties. The process of the invention, which has been called "particle smoothing", makes it possible to alter the surface characteristics of the carrier particles for inhalation use, without causing their agglomeration into granules or pellets, and is explained in detail in the examples given below. As a result of this smoothing process, a powder is obtained that consists of individual particles. Moreover, the process only gives rise to a slight reduction of the particle size relevant to the starting product, without increasing the fraction of fine particles. The carrier of the invention, consisting of individual smooth particles, is therefore clearly different from carriers in which the particles are agglomerated to form pellets, i.e. granular shapes obtained by agglomerating several individual particles together, as those described in WO 95/24889, WO 95/09615, WO 95/09616.

The method of the invention is rapid and convenient, and produces particles with smooth surfaces with rounded edges and corners, eliminating from their surface the asperities and clefts originally present, i.e. high-energy sites on which the active particles can strongly adhere. Furthermore, as a result of the claimed process that consists of stages of wetting and slow drying, as will be explained in more detail later, the fine particles present in the powder prior to be smoothed are eliminated from the final product. The method of the invention therefore makes it possible to eliminate the small random differences that are inherent to the industrial manufacturing process, and are detrimental to their efficiency when they are used as carriers for inhalation powders.

A further advantage of the method of the invention is that it makes possible to obtain particles that are perfectly smooth and are therefore characterized by a very low surface rugosity, starting from particles with a coarser particle size, for instance between 30 and 600 μm (preferably between 90 and 150 μm).

The smoothing process is carried out in repeated stages of wetting with a solvent and drying of the carrier particles. For wetting the particles an aqueous or aqueous-alcoholic solution is preferably used, and the powder particles are caused to roll on the walls of the mixing chamber as it is submitted to rapid mixing by the rotating paddle of the high-speed granulator. Photographs taken with the scanning electron microscope (SEX, if samples of lactose particles taken at the beginning (a), curing (b and c) and at the end (d) of the smoothing process, are shown (FIG. 1). This method leads to surface smoothing of the lactose particles, eliminating the sharp edges and any fissures, without significantly changing the size and shape of the particles. The method also leads to elimination of the fraction of fine particles that were present in the original powder. The graphs in FIG. 1, superimposed on the images of the particles, provide a quantitative evaluation of the change in rugosity as a result of the smoothing process, by means of an image analysis system applied to the photographs of the particles. This approach makes it possible to measure, on the surface of the particles, the variation in level of grey as a function of position (the region measured for each particle is indicated by the shaded rectangle reproduced in the Figure). The surface rugosity of the particles is quantified from the deviation from linearity of the lines reproduced in the diagram, which relate to the variation in grey level of the image relating to the surface of the particle. The smoother is the particle, the more uniform is the level of grey of its image, and hence more straight is the line. Quantitative measurement of rugosity can be obtained from measurement of the fractal dimension of this line which expresses the level of grey as a function of the position on the surface of the crystal (fractal scale). The more this line moves away from a straight line, the more the value of the fractal dimension is different from that of the topological dimension, which is the unity for a straight line. The fractal dimension of the smooth particles is indeed equal to one, as explained by B. H. Kaye (Part. P

TABLE 1

| Stages of processing | Fractal dimension |
|---|---|
| Starting lactose | 1.23 |
| Step #1 | 1.08 |
| Step #7 | 1.06 |
| Smoothed lactose | 1 |

Table 1 shows the values of fractal dimension corresponding to the "rugosity" lines shown in FIG. 1, according to the various stages of smoothing indicated. The particles are considered to be acceptably smooth when the fractal dimension is ≦1.1.

Surface smoothing, redistribution of the fraction of fine particles in the fissures and rounding of the edges are obtained by a mechanism of controlled solubilization and deposition of the lactose, due to wetting with the solvent sprayed on the powder followed by slow drying, while the mixture is submitted to rapid mixing. Since the chamber of the mixer is of cylindrical shape and the rotating paddle (impeller) is positioned centrally at the base of the chamber, the powder is caused to roll on the walls of the said chamber. During this rolling, rounding of the edges of the individual particles occurs, without causing any agglomeration of the particles on account of the choice of type and amount of solvent used. The surface characteristics of the carrier particles are a direct consequence of the method of treatment. The final result is the reduction or elimination of the high-energy sites from the surface of the particles, which arise in the original operations of manufacturing of the carrier. Smoothing the lactose particles by means of the method of the invention makes it possible to obtain a carrier for inhalation powders of higher performances with respect to the respirable fraction of drug, in comparison with powder that has not been smoothed.

Another aspect of the present invention relates to the preparation of smooth powders for inhalation purposes using a solution or suspension of the carrier in a liquid containing a suitable additive with properties such as to promote disaggregation of the drug from the surface of the carrier during inhalation. With respect to the prior art, the process of the invention permits to achieve an at least partial coating of the carrier particles in liquid phase. Advantageously during the smoothing process, the particles of additive are trapped on the surface of he carrier particles, forming a coating capable of modulating the drug-carrier interparticle forces. By virtue of said process, the particles of additive are firmly bound to the surface of the carrier. As a consequence, during inhalation, the particles of additive are deposited together with the coarse carrier particles in the oropharyngeal cavity, so they are not inhaled.

DESCRIPTION OF THE PREFERRED CONDITIONS

The carrier particles can be made of any physiologically acceptable, inert material. Preferred carriers are those consisting of crystalline sugars such as glucose, mannose, galactose, sorbitol, mannitol, lactose, saccharose, trehalose, raffinose, cyclodextrins and mixtures thereof. Carriers comprising α-lactose monohydrate are even more preferred. The particles of the carrier can have a size between 30 and 600 μm, preferably between 90 and 150 μm.

To carry out the process of the invention, high-speed mixer-granulators such as the Roto J Zanchetta (Zanchetta S. p. A. Lucca), or the Diosna P50 (Dierksohne, Osnabruck, Germany) can be advantageously used.

Short-chain aliphatic alcohols, or water-alcohol mixtures, can be used advantageously as solvents. The preferred conditions envisage the use of a water:alcohol mixture from 9:3 to 3:4 v/v; more preferred conditions are those in which the water:ethanol ratio is 5:3 v/v; even more preferred are those in which the ratio is 3:3 v/v.

The optimum ratio between volume of solution and amount of carrier to be smoothed is between 5 ml/100 g and 70 ml/100 g, preferably 53 ml/100 g.

The operating conditions of the high-speed mixer-granulator are: rotary speed of the mixing paddle (impeller) between 25 and 600 rev/min; temperature of the outer jacket of the mixing chamber between 20° C. and 90° C., preferably 50° C.; solution nebulization pressure between 1 and 10 bar, preferably 3.5 bar; diameter of the nebulization nozzle between 0.7 and 20 mm, preferably 1.0 mm; vacuum inside the mixing chamber between −0.2 and −0.8 bar, preferably −0.7 bar.

The total mixing time of the carrier powder particles during smoothing is preferably comprised between 120 and 300 minutes, with a period of drying, after each stage of spraying of the smoothing solution, of between 10 and 30 minutes.

The additives can be selected from those belonging to the class of lubricants, such as magnesium stearate, sodium benzoate, sodium stearylfumarate or to the class of anti-adherents such as leucine and isoleucine. Other additives that can be advantageously used are soluble polymers such as hydroxyethylcellulose, methylcellulose, carboxymethylcellulose, polyvinylpyrrolidone, polyethyleneglycol, cyclodextrins.

With respect to the volume of the solution, the additive is added in amounts preferably between 0.05% and 2%, more preferably between 0.25% and 1%, even more preferably 0.45%

The final formulation should contain from 0.1 to 10 by weight of a lubricant, more preferably 0.25% by weight of magnesium stearate.

The spraying times of the solution or suspension of additive are between 5 and 30 seconds.

The inhalation formulations that can be obtained by mixing active principles in the form of micronized powder (median diameter≦6.4 μm) with carrier powders obtained by the claimed method constitute a further object of the invention.

Preferred active ingredients are the drugs usually administered in micronized form for the treatment of respiratory diseases by inhalation, for example steroids such as beclometasone dipropionate, flunisolide and budesonide, β-agonists such as salbutamol, formoterol, salmeterol, terbutaline, their salts and mixtures thereof, anticholinergics such as ipratropium bromide and oxitrtopium bromide. However, any active principle suitable for endobronchial administration can be used.

The process of the invention is illustrated in detail by the examples that follow, which do not limit its application in any way.

FIG. 1 and Table 1 give the fractal dimensions relating to particle surface rugosity of α-lactose monohydrate before, during and at the end of smoothing.

EXAMPLE 1

Inhalation Powder Made of Beclometasone Dipropionate (BDP) Mixed with Smoothed α-lactose Monohydrate Carrier Method of Manufacture a) The carrier particles of the invention were prepared as follows:

750 g of lactose α-monohydrate (size fraction 90–150 μm) was loaded into the high-speed granulator (Zanchetta Roto Junior, Lucca, I), with the heating jacket at a temperature of 50° C. and with vacuum of −0.7 bar. After starting the mixing impeller at a speed of 50 rev/min, 40 ml of a 3:5 v/v mixture of ethyl alcohol:distilled water was sprayed on the powder for a time of 10 seconds. After completion of the spraying stage, the speed of the mixing impeller was increased to 450 rev/min for 15 minutes, in order to cause the powder particles to roll along the circular wall of the mixer and promote drying of the said powder particles. The stages of spraying and drying, as described, were repeated 10 times, until a total solution volume of 400 ml was added.

b) At the end of the smoothing stage, the powder was removed from the mixer chamber and was placed in an air-circulation stove for 240 minutes at 60° c.

c) Afterwards, the dried powder particles were placed and kept in a climate chamber at a temperature of 20° C. and 60% RH. The smoothed lactose particles, photographed using a scanning electron microscope, were found to possess a morphology with rounded corners and a smooth surface, as can be seen in FIG. 1, which shows the variation in rugosity of the lactose particles during the smoothing stages.

The size of the lactose particles before and after smoothing, expressed as geometric mean diameter ($d_g$) and geometric standard deviation ($\sigma_g$) had not been altered substantially:

| | | |
|---|---|---|
| starting lactose | $d_g$: 123.9 μm; | $\sigma_g$: 1.05 |
| lactose after smoothing | $d_g$: 119.3 μm; | $\sigma_g$: 1.10 |

The rugosity factor calculated by SEM is reported in Table 1.

The rugosity factor was also calculated according to Ganderton (BG 2 240 237), i.e. by calculating the ratio between the specific surface area, determined by air permeametry and the geometric specific surface area.

The results are reported in Table 2.

TABLE 2

| Composition | Rugosity Factor |
|---|---|
| BDP/lactose | 2.7 |
| BDP/smoothed lactose | 2.4 |

The results demonstrate that using the specific surface area obtained by the air permeametry method described in GB 2 240 237, no difference between the original and the smoothed lactose can be detected. Moreover, in both cases, using as a starting carrier particles of size greater than 90 μm, the rugosity factor turned out to be greater than 1.75, which is the upper limit value of the aforementioned patent. In order to check for potential change in the crystalline structure, powder X-ray diffraction and differential scanning calorimetry analysis were carried out on the starting lactose and on the smoothed lactose. Both the thermal and diffraction patterns demonstrated that the crystalline structure of the lactose had not been changed by the process of smoothing.

d) The inhalation powder, consisting of a drug/carrier mixture, was prepared as follows:

0.684 g of BDP was mixed with 80 g of smoothed lactose, in three different steps:

i. pre-mixing for 10 minutes of the whole amount of BDP with approx. 9/10 of the carrier, in a rotating-chamber mixer (Turbula®), using a cylindrical steel container with volume of approx. 300 ml;

ii. disaggregation of the aggregates on a metal screen with 300 μm holes;

iii. "washing" of the screen used for disaggregation with the remainder of the carrier and mixing of all the combined powder for 30 minutes in the steel container of the Turbula® mixer.

The dose of inhalation mixture that was loaded in the inhaler for delivery was made up of 24.8 mg of carrier and 0.2 mg of BDP.

Monitoring of the Respirable Fraction of the Inhalation Powder

A quantity of inhalation powder was loaded in a Pulvinal® powder inhaler (Chiesi Farmaceutici, Italy) and kept in a climate chamber at 20° C. and 60% RH for about 3 days before starting each aerosolization test.

The respirable fraction of the inhalation powder prepared according to Example 1 was evaluated using a twin-stage impinger (Apparatus of type A for the aerodynamic evaluation of fine particles described by the FU IX, 4th supplement 1996). The instrument is made of various glass components, connected together to form two chambers capable of separating the inhalation powder as a function of its aerodynamic dimensions, called the upper separating chamber (Stage 1) and the lower separating chamber (Stage 2). A rubber adapter provides connection to the Pulvinal® inhaler that contains the dose of inhalation powder. The apparatus is connected to a vacuum pump that produces a flow of air through the separating chambers and the inhaler connected to them. During the delivery stage, the differences in shape and size of the particles of the inhalation powder, as well as the air stream, cause discrete deposition of the particles in the separating chambers. Inserting the inhaler in the appropriate rubber adapter and applying an air flow of 60 l/min for 10 seconds (a flow that reproduces the inspiratory capacity of an asthmatic patient), it was possible to separate the particles of the powder delivered in the two stages of the apparatus (Stage 1 and Stage 2). The limit value of aerodynamic diameter, $d_{ae}$, for deposition in the lower separating chamber is 6.4 μm. Particles with larger $d_{ae}$ are deposited in Stage 1 and particles with smaller $d_{ae}$ in Stage 2. A minimum volume of solvent is present in both stages (30 ml in Stage 2 and 7 ml in Stage 1), consisting of an acetonitrile:water mixture 6:4 v/v, to prevent impaction of the particles on the apparatus walls and to facilitate their recovery.

After nebulization of a dose of powder in the twin-stage impinger, the apparatus i dismantled and the quantities of drug deposited in the two separating chambers are recovered by washing with solvent mixture and brought up to a volume of 100 ml in two graduated flasks, one for Stage 1 and one for Stage 2, respectively. The quantities collected in the two flasks are then analysed.

Results

The results relating to determination of the respirable fraction are given in Table 3 in comparison with a similar preparation obtained by mixing BDP and unsmoothed lactose (reference preparation). The respirable fraction is expressed as the percentage of particles of active principle found in Stage 2 relative to the quantity of active principle delivered.

The results demonstrate a significant increase in respirable fraction.

TABLE 3

| Composition | Respirable fraction (%) |
|---|---|
| BDP/lactose | 9.0 ± 1.0 |
| BDP/smoothed lactose | 21.8 ± 2.7 |

EXAMPLE 2

Inhalation Powder of Beclometasone Dipropionate Mixed with Smoothed α-lactose Monohydrate Carrier in the Presence of Isoleucine a) The carrier particles of smoothed lactose in the presence of isoleucine were prepared as described in Example 1 (a), coating the particles using an aqueous-alcoholic solution (5:3 v/v) containing isoleucine equal to 0.75% of the amount of lactose used. FIG. 2 shows the smoothed particles and graphic evaluation of their rugosity.

b) The inhalation powder was prepared by missing BDP with smoothed lactose in the presence of isoleucine according to the method described in Example 1 (d).

c) Determination of the respirable fraction of the prepared mixture was effected using the Pulvinal® powder inhaler, in accordance with the method described in Example 1.

The results are given in Table 4.

The results show that there is a significant increase in respirable fraction, as well as with respect to the preparation containing smoothed lactose with no additive (Table 3).

TABLE 4

| Composition | Respirable fraction (%) |
|---|---|
| BDP/lactose | 9.0 ± 1.0 |
| BDP/smoothed lactose with isoleucine | 30.5 ± 2.8 |

EXAMPLE 3

Inhalation Powder of Beclometasone Dipropionate Mixed with Smoothed α-lactose Monohydrate Carrier in the Presence of Magnesium Stearate a) The carrier particles of smoothed lactose in the presence of magnesium stearate were prepared as described in Example 1 (a), coating the particles using an aqueous-alcoholic suspension (5:3 v/v) containing magnesium stearate equal to 0.25% of the amount of lactose used. FIG. 3 shows the smoothed particles and graphical evaluation of their rugosity. The microscope images also demonstrate absence of fine particles adhering to the surface of the smoothed crystal of lactose, indicating that the particles of magnesium stearate remain trapped on the smoothed surface.

b) The inhalation powder was prepared by missing BDP with smoothed lactose in the presence of magnesium stearate according to the method described in Example 1 (d).

c) Determination of the respirable fraction was effected using the Pulvinal® powder inhaler, in accordance with the method described in Example 1.

The results are presented in Table 5. Also in this case, a significant increase in respirable fraction was observed, as well as with respect to the preparation containing smoothed lactose with no additive.

TABLE 5

| Composition | Respirable fraction (%) |
|---|---|
| BDP/lactose | 9.0 ± 1.2 |
| BDP/smoothed lactose with magnesium stearate | 31.0 ± 1.8 |

EXAMPLE 4

Inhalation Powder of Beclometasone Dipropionate Mixed with Smoothed α-lactose Monohydrate Carrier in the Presence of Magnesium Stearate Performances at Different Air Flows a) The carrier particles of the invention were prepared as follows:

a) 750 g of lactose α-monohydrate (size fraction 90–150 μm) was loaded into the high-speed granulator (Zanchetta Roto Junior, Lucca, I), with the heating jacket at a temperature of 50° c. and with vacuum of −0.7 bar. After starting the mixing impeller at a speed of 50 rev/min, 40 ml of a 1:1 v/v mixture of ethyl alcohol:distilled water, containing magnesium stearate equal to 0.25% of the amount of lactose used, was sprayed on the powder for a time of 10 seconds. After completion of the spraying stage, the speed of the mixing impeller was increased to 450 rev/min for 15 minutes, in order to cause the powder particles to roll along the circular wall of the mixer and promote drying of the said powder particles. The stags of spraying and drying, as described, were repeated 10 times, until a total solution volume of 400 ml was added.

b) At the end of the smoothing stage, the powder particles were removed from the mixer chamber and was placed in an air-circulation stove for 240 minutes at 60° C.

c) Afterwards, the dried powder was placed and kept in a climate chamber at a temperature of 20° C. and 60% RH.

d) the inhalation powder was prepared by missing BDP with smoothed lactose in the presence of magnesium stearate according to the method described in Example 1 (d).

e) Determination of the respirable fraction of the prepared mixture was carried out using the Pulvinal® powder inhaler, in accordance with the method described in Example 1. The respirable fraction was also determined after applying an air flow of 30 l/min.

The results are given in Table 6, in comparison with the reference preparation. The results show that there is a significant increase in respirable fraction at both air flows. This allows the powder of the invention to be used with medium-resistance as well as high-resistance dry powder inhalers.

TABLE 6

| Composition | Respirable fraction (%) (30 L/min) | Respirable fraction (%) (60 L/min) |
|---|---|---|
| BDP/lactose | — | 9.0 ± 1.0 |
| BDP/smoothed lactose with magnesium stearate | 62.7 ± 1.0 | 68.6 ± 1.5 |

EXAMPLE 5

Inhalation Powder of Low Beclometasone Dipropionate Dose Mixed with Smoothed α-lactose Monohydrate Carrier in the Presence of Magnesium Stearate a) The carrier particles of smoothed lactose in the presence of magnesium stearate were prepared as described in Example 4 (a).

b) 0.068 g of BDP was mixed with 80 g of smoothed lactose in presence of magnesium stearate, in three separate steps:

i. pre-mixing for 10 minutes of the whole amount of BDP with approx. 9/10 of the carrier, in a rotating-chamber mixer (Turbula®), using a cylindrical steel container with volume of approx. 300 ml;

ii. disaggregation of the aggregates on a metal screen with 300 μm holes;

iii. "washing" of the screen used for disaggregation with the remainder of the carrier and mixing of all the combined powder for 60 minutes in the steel container of the Turbula® mixer.

The dose of inhalation mixture that was loaded in the inhaler for delivery was made up to 24.98 mg of carrier and 0.02 mg of BDP.

c) Determination of the respirable fraction of the prepared mixture was effected using the Pulvinal® powder inhaler, in accordance with the method described in Example 1.

The results ae given in Table 7, in comparison with the reference preparation. The results show that there is a significant increase in respirable fraction and therefore the process of the invention is also suitable for preparing powders for inhalation containing low-strength active ingredients.

TABLE 7

| Composition | Respirable fraction (%) |
| --- | --- |
| BDP low dose/smoothed lactose with magnesium stearate | 46 ± 12.4 |

What is claimed is:

1. A carrier for micronized drugs comprising a plurality of particles, said plurality of particles coated with an additive selected from the group consisting of lubricants, anti-adherents and soluble polymers; wherein said plurality of particles has a median diameter of greater than 90 µm and a surface rugosity expressed as the fractal dimension of less than or equal to 1.1.

2. The carrier as claimed in claim 1, wherein the plurality of particles is a plurality of partially coated particles.

3. The carrier as claimed in claim 1, wherein the carrier comprises one or more saccharides selected from the group consisting of glucose, mannose, galactose, sorbitol, mannitol, lactose, saccharose, trehalose, raffinose and cyclodextrins.

4. The carrier as claimed in claim 1, wherein the plurality of particles comprise α-lactose monohydrate.

5. The carrier as claimed in claim 1, wherein the plurality of particles has a particle size between 90 and 150 µm.

6. The carrier as claimed in claim 1, wherein the lubricant is magnesium stearate, sodium benzoate, or sodium stearyl fumarate.

7. The carrier as claimed in claim 1, wherein the anti-adherent is leucine or isoleucine.

8. The carrier as claimed in claim 1, wherein the soluble polymer is hydroxyethylcellulose, methylcellulose, carboxymethylcellulose, polyvinylpyrrolidone, polyethyleneglycol, or cyclodextrins.

9. A process for preparing the carrier as claimed in claim 1, said process comprising subjecting a plurality of particles having a median diameter of greater than 90 µm to repeated stages of wetting with a solvent, wherein the additive is dissolved or dispersed in said solvent, and drying.

10. The process as claimed in claim 9, comprising carrying out the repeated stages of wetting and drying in a high-speed granulator, said high-speed granulator consisting of a cylindrical mixing chamber (container) comprising a rotating paddle (impeller) and a spray nozzle, wherein said high-speed granulator is capable of operating at controlled temperature and pressure.

11. The process according to claim 10, wherein a mixing time is between 120 and 300 minutes.

12. The process according to claim 9, wherein a carrier substantially free from fine particles with a particle size of less than 10 µm is obtained.

13. The process according claim 9, wherein the additive is present in an amount between 0.05 and 2%.

14. A powder pharmaceutical composition for inhalation comprising the carrier as claimed in claim 1 and a micronized active substance.

15. The powder pharmaceutical composition for inhalation as claimed in claim 14, wherein the micronized active substance has a median particle diameter less than or equal to 6.4 µm.

16. The powder pharmaceutical composition for inhalation as claimed in claim 14, wherein said micronized active substance is a β-agonist.

17. The powder pharmaceutical composition for inhalation as claimed in claim 16, wherein the β-agonist is salbutamol, formoterol, salmeterol, terbutaline, salts thereof or epimers thereof.

18. The powder pharmaceutical composition for inhalation as claimed in claim 14, wherein said micronized active substance is an anti-inflammatory steroid.

19. The powder pharmaceutical composition for inhalation as claimed in claim 18, wherein the anti-inflammatory steroid is beclometasone dipropionate, flunisolide, bedesonide or epimers thereof.

20. The powder pharmaceutical composition for inhalation as claimed in claim 14, wherein the micronized active substance is an anticholinergic.

21. The powder pharmaceutical composition for inhalation as claimed in claim 20, wherein the anticholinergic is ipratropium bromide or oxitropium bromide.

22. An inhalable pharmaceutical composition comprising the carrier as claimed in claim 1, and a drug in the form of a micronized powder.

* * * * *